United States Patent [19]
Babaev

[11] Patent Number: 5,611,993
[45] Date of Patent: Mar. 18, 1997

[54] ULTRASONIC METHOD OF TREATING A CONTINUOUS FLOW OF FLUID

[75] Inventor: Eilaz P. O. Babaev, Hopkins, Minn.

[73] Assignee: Areopag USA, Inc., Minneapolis, Minn.

[21] Appl. No.: 519,389

[22] Filed: Aug. 25, 1995

[51] Int. Cl.⁶ ............................... A61L 2/02; C02F 1/36
[52] U.S. Cl. ........................ 422/20; 422/128; 210/748; 204/158.2
[58] Field of Search ........................ 422/20, 39, 128; 210/748; 366/127; 204/157.15, 157.42, 157.62, 158.2; 588/227

[56] References Cited

U.S. PATENT DOCUMENTS

| | | | |
|---|---|---|---|
| 2,417,722 | 3/1947 | Wolff | 422/20 |
| 2,578,505 | 12/1951 | Carlin | 210/748 |
| 2,585,103 | 2/1952 | Fitzgerald | 210/748 |
| 2,717,874 | 9/1955 | Verain | 422/20 |
| 4,086,057 | 4/1978 | Everett | 422/128 |
| 4,168,295 | 9/1979 | Sawyer | 422/128 |
| 4,477,357 | 10/1984 | Sittenfield | 422/20 |
| 4,944,886 | 7/1990 | Masri | 210/748 |
| 4,961,860 | 10/1990 | Masri | 422/20 |
| 5,198,122 | 3/1993 | Koszalka et al. | 210/748 |
| 5,395,592 | 3/1995 | Bolleman et al. | 422/128 |

OTHER PUBLICATIONS

Aqueous Cleaning Systems, by Crest Ultrasonics.
Aqueous Ultrasonic Cleaning, by Branson Ultrasonics Corporation, 1988.
Ultrasonic Cleaning Equipment for Ultimate Cleaning Power, by Crest Ultrasonics.
Bransonic® Ultrasonic Benchtop Cleaners, by Branson Ultrasonics Corporation, 1993.
Ultrasonic Cleaning Systems, by Blue Wave Ultrasonics.
Ultrasonics, McGraw–Hill Encyclopedia of Science & Technology, 6th Edition, vol. 19 ULC–ZYT, pp. 7–15, 1987.
Cavitation, McGraw–Hill Encyclopedia of Science & Technology, 6th Edition, vol. 3 BOR–CLE, pp. 302–305, 1987.

*Primary Examiner*—Robert J. Warden
*Assistant Examiner*—Theresa T. Snider
*Attorney, Agent, or Firm*—Kinney & Lange, P.A.

[57] ABSTRACT

A method for sterilizing a continuous flow of wastewater containing bacteria includes applying high frequency sound waves to the continuous flow of wastewater to cause cavitation in the wastewater.

9 Claims, 7 Drawing Sheets

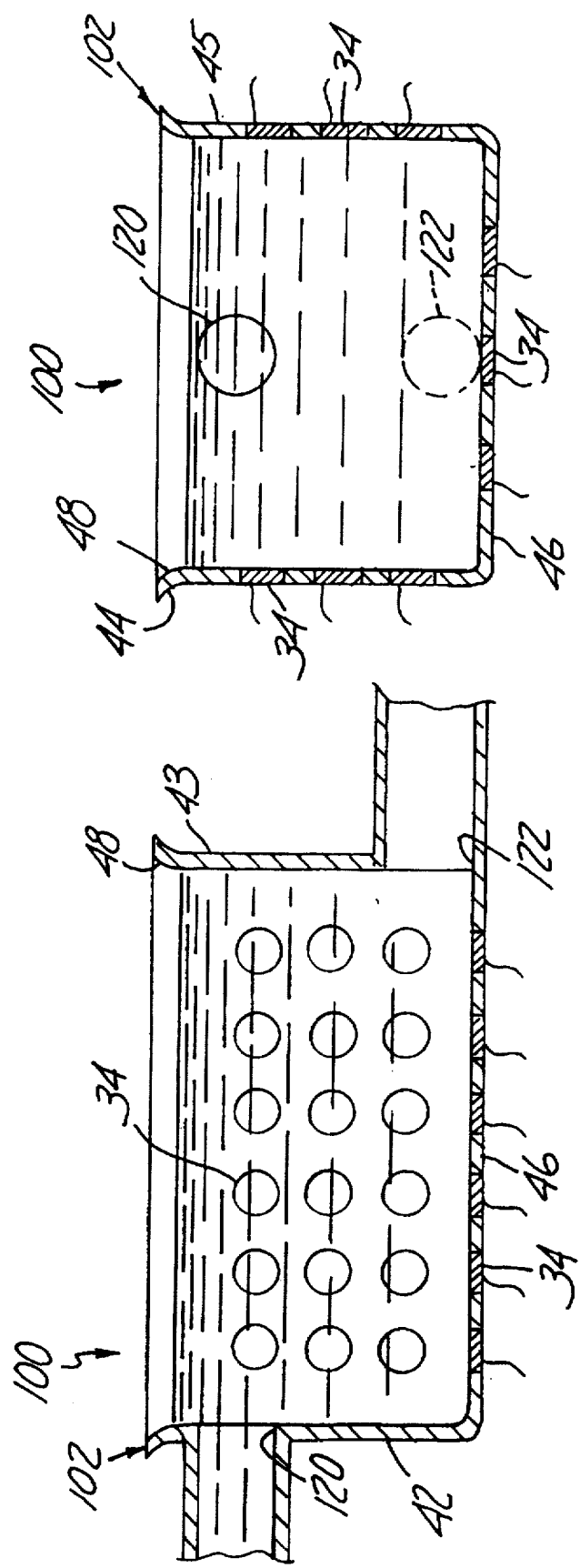

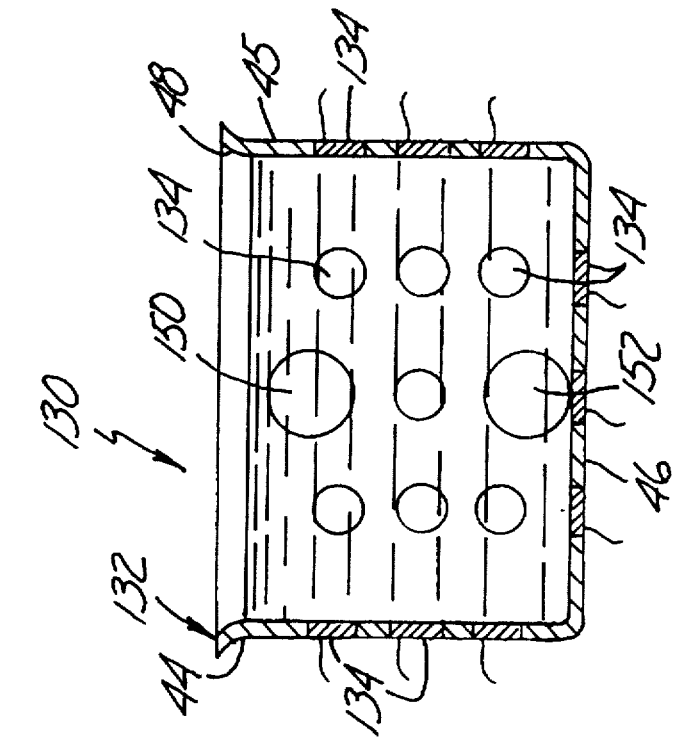

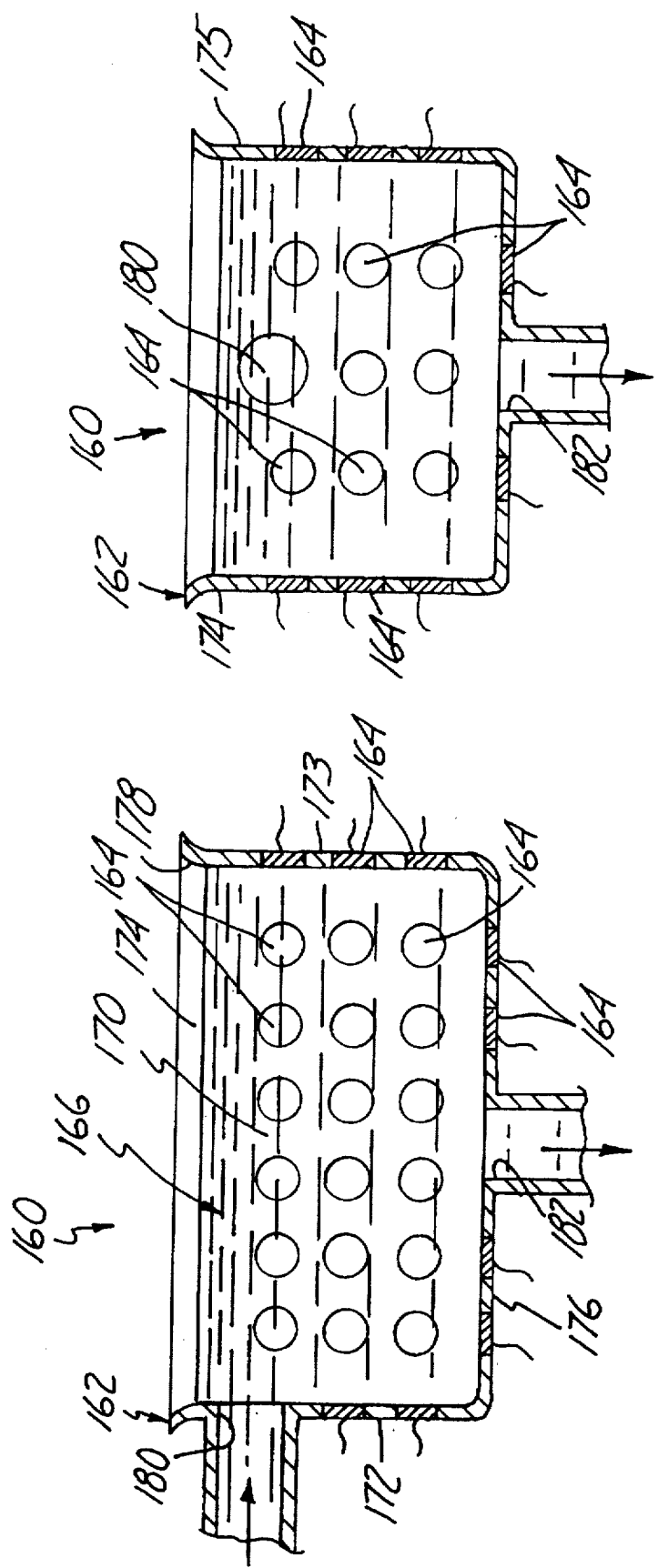

ULTRASONIC METHOD OF TREATING A CONTINUOUS FLOW OF FLUID

BACKGROUND OF THE INVENTION

The present invention relates to a method and apparatus for treating and sterilizing a continuous flow of wastewater and a method and apparatus for catalyzing a chemical reaction in a continuous flow of liquid. In particular, the present invention relates to applying ultrasonic energy to a continuous flow of wastewater to sonicate and thereby sterilize the wastewater. The present invention also relates to applying ultrasonic energy to a continuous flow of liquid to selectively catalyze a chemical reaction in the liquid.

Many of today's chemical, metallurgical and food production processes produce extremely large volumes of chemically and bacteriologically contaminated or polluted water. For example, a food manufacturing plant processing potatoes may produce as many as two million gallons of wastewater per day. As a result, it is extremely difficult and expensive to contain the wastewater in a single containment structure. Thus, it is necessary to treat a continuous flow of the wastewater as the wastewater is discharged from the manufacturing or production facility.

Chemically contaminated water typically includes ammonium, petroleum, ethel and other hydrocarbons. Chemically-polluted water is typically cleaned to remove chemicals from the water by bacteriological means. However, this approach to treating chemically-polluted water results in an alternative problem, bacteriologically polluted wastewater.

Bacteriologically polluted wastewater typically contains various bacteria such as Pseudomonas aeruginosa, staphylococcus, E. coli, molds and other types of bacteria. Unless treated before being released, bacteriologically polluted water pollutes the environment and may lead to irreversible damage to bodies of water such as rivers and lakes as well as the plants and animals dependent upon the bodies of water.

Bacteriologically polluted wastewater is conventionally treated by sterilizing or killing the bacteria with chlorine dioxide. Unfortunately, chlorine dioxide itself may also be hazardous to the environment. As a consequence, the use of chlorine dioxide to sterilize bacteriologically polluted wastewater is highly regulated and limited by pollution control agencies such as the United States Environmental Protection Agency. Because the concentration of chlorine dioxide used for treating wastewater is limited, chlorine dioxide is not completely effective for sterilizing and treating bacteriologically polluted wastewater. For example, at the current chlorine dioxide concentration level allowed by the Environmental Protection Agency, treatment processes relying upon chlorine dioxide for treating bacteriologically polluted wastewater are capable of killing only approximately 20% of the bacteria within the wastewater.

Sound waves having frequencies above the audible range, i.e. above about 20 kilohertz, are commonly referred to as ultrasonic waves. Ultrasonic waves are currently used in a wide variety of engineering applications including both low-amplitude applications and high-amplitude applications. Low-amplitude ultrasonic applications capitalize upon the changes that boundaries and imperfections in the materials cause in wave propagation properties of the ultrasonic waves. Examples of low-amplitude applications for ultrasonic sound waves include sonar, the measurement of elastic constants of gases, liquids and solids, the measurement of the attenuation of sound waves and the measurement of acoustic emissions. Low-amplitude ultrasonic sound waves are also used in a multitude of ultrasonic devices such as mechanical filters, inspectrascopes, thickness gauges, delay lines and surface acoustic-wave devices.

High-amplitude applications of ultrasonic sound waves (macrosonics) capitalize upon a process known as cavitation. Cavitation occurs when the high-amplitude ultrasonic sound waves create holes or gas-bubble cavities in a liquid. When each cavity collapses, extremely high pressures or forces are generated by high amplitude sound waves produced in the liquid. These extremely high pressures and large acoustic forces are used for a variety of applications.

It is conventional wisdom that, to effectively utilize the extremely high pressures and large acoustic forces in the liquid, the liquid in which cavitation is produced must be stationary and contained. As a result, high-amplitude ultrasonic sound waves are typically utilized in batch processes and batch receptacles containing stationary, fixed volumes of liquid. For example, high-amplitude ultrasonic sound waves are frequently used for cleaning and fatigue testing of metal parts and for sterilizing surgical instruments submersed in liquid stationarily contained in tanks. High-amplitude ultrasonic waves are also utilized for sterilizing the liquid itself such as milk and water. For example, in laboratory settings, probes producing ultrasonic sound waves are inserted into small, limited and highly controlled volumes of water contained in a test tube or similar receptacle to sterilize the water for highly controlled experiments. Each of the processes employing high-amplitude ultrasonic sound waves typically employs a batch receptacle containing a controlled volume of liquid to which ultrasonic energy (i.e. ultrasonic sound waves) is applied. However, high-amplitude ultrasonic waves have not been utilized with continuous flows of liquid since the conventional wisdom is that high-amplitude ultrasonic sound waves are not effective in applications involving a continuous flow of liquid such as the continuous flow of wastewater typically produced by today's chemical, metallurgical, and food production processes.

SUMMARY OF THE INVENTION

The present invention is a method and apparatus for treating a continuous flow of wastewater containing bacteria. The method includes applying high frequency sound waves (waves having a frequency greater than approximately 10 kilohertz) to the continuous flow of wastewater to cause cavitation in the wastewater. The application of high frequency sound waves to the continuous flow of wastewater kills bacteria within the wastewater to minimize or eliminate the need for chemical treatment of the wastewater by such chemicals as chlorine dioxide before the continuous flow of wastewater is discharged or reused. The method may also be used to catalyze a chemical reaction in a continuous flow of liquid to eliminate the need for a separate catalyst.

The apparatus includes a fluid passage through which the continuous flow of wastewater passes. The apparatus further includes at least one high frequency sound wave transducer in a coupled relationship to the fluid passage for transmitting high frequency sound waves to the continuous flow of wastewater. The preferred embodiments of the apparatus include various configurations and outlet and inlet locations to promote temporary pooling of the wastewater within the fluid passage to increase the effectiveness at which the apparatus kills bacteria within the wastewater.

BRIEF DESCRIPTION OF THE DRAWINGS

FIG. 4A is a cross-sectional view of an alternate embodiment of the system.

FIG. 4B is a cross-sectional view of the system of FIG. 4A.

FIG. 5A is a cross-sectional view of an alternate embodiment of the system.

FIG. 5B is a cross-sectional view of the system of FIG. 5A.

FIG. 6A is a cross-sectional view of an alternate embodiment of the system.

FIG. 6B is a cross-sectional view of the system of FIG. 6A.

DETAILED DESCRIPTION OF THE PREFERRED EMBODIMENTS

Figure 1B:
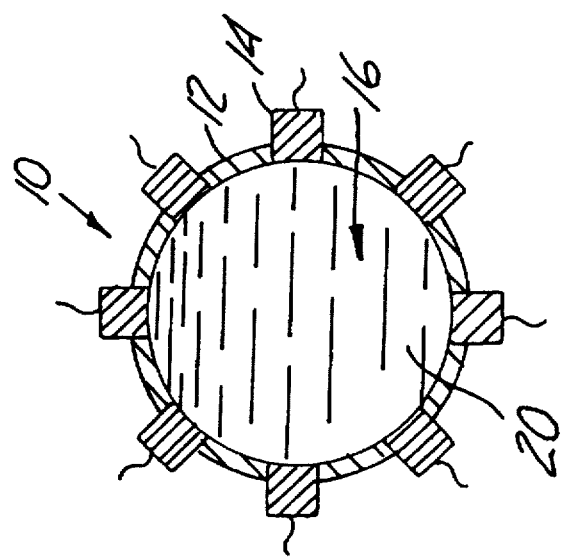
FIG. 1B is a cross-sectional view of the system of FIG. 1A.
Figure 1A:
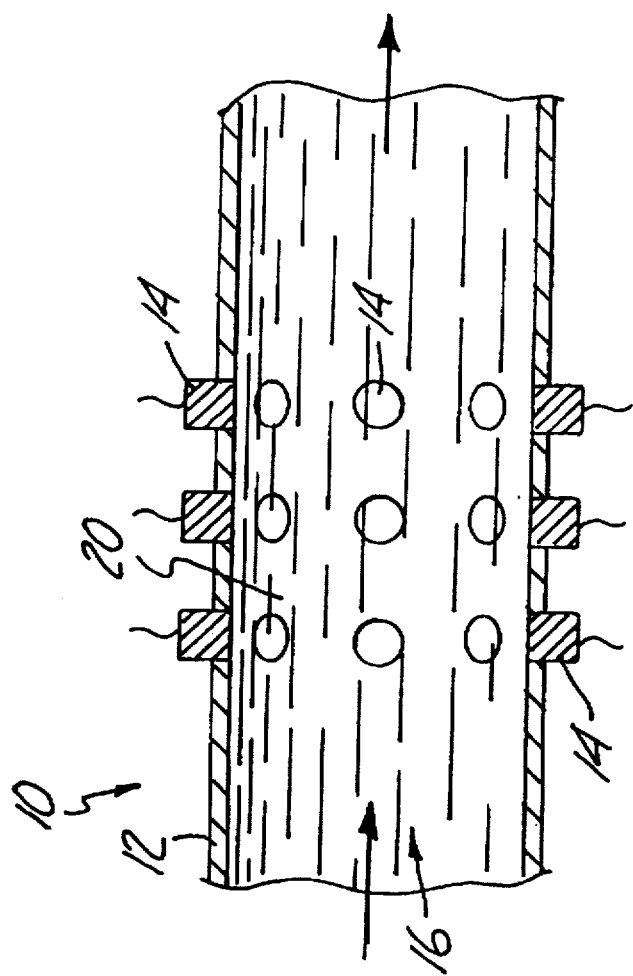
FIG. 1A is a cross-sectional view of a system for sterilizing a continuous flow of wastewater.

FIGS. 1A and 1B illustrate system 10 treating and sterilizing a continuous flow of wastewater utilizing high-frequency sound waves. System 10 includes a conduit or pipe 12 and sound wave transducers 14. Pipe 12 defines a fluid passage 16 having a sterilization region 20. Fluid passage 16 channels and directs a continuous flow of wastewater through and across sterilization region 20. Sterilization region 20 is a region in which the continuous flow of wastewater is sterilized.

It has been discovered that the emission of sound waves having a frequency of between about 10 kilohertz to about 200 kilohertz through a continuous flow of wastewater is capable of killing bacteria within the continuous flow of wastewater to sterilize the wastewater. It has further been discovered that sound waves emitted at a frequency of 20 kilohertz to about 40 kilohertz (20 kilohertz being the optimal) kill the largest percentage of bacteria in the continuous flow of wastewater. In recognition of this discovery, sterilization region 20 is provided with high frequency sound wave transducers 14 to sterilize and treat the continuous flow of wastewater which previously required chlorine dioxide for treatment.

Sound wave transducers 14 are well-known in the art and emit high frequency sound waves. For purposes of this application, high-frequency sound waves include all sound waves having a frequency of between about 10 kilohertz and 200 kilohertz. Transducers 14 preferably extend through a side wall of pipe 12 so as to be adjacent to sterilization region 20 of flow passage 16 within pipe 12. Transducers 14 circumferentially extend about at least a portion of pipe 12. Preferably, transducers 14 circumferentially extend about an entire circumference of pipe 12 circumjacent region 20. Because transducers preferably extend about at least a portion of pipe 12, transducers 14 emit high frequency sound waves through the continuous flow of waste water in a plurality of different directions. Because transducers 14 emit high frequency sound waves from a plurality of different directions through the continuous flow of wastewater, cavitation within the continuous flow of wastewater is increased to more effectively kill bacteria. To further increase the effectiveness of system 10 in killing bacteria within the continuous flow of wastewater, the power level or output of transducers 14 and the flow rate of the continuous flow of wastewater are preferably controlled or regulated so that the continuous flow of wastewater is exposed to the high frequency sound waves emitted from transducers 14 in sterilization region 20 for a sufficient amount of time to adequately kill the bacteria in the wastewater depending upon the desired bacteria levels of the treated water exiting sterilization region 20 of system 10.

Figure 2B:
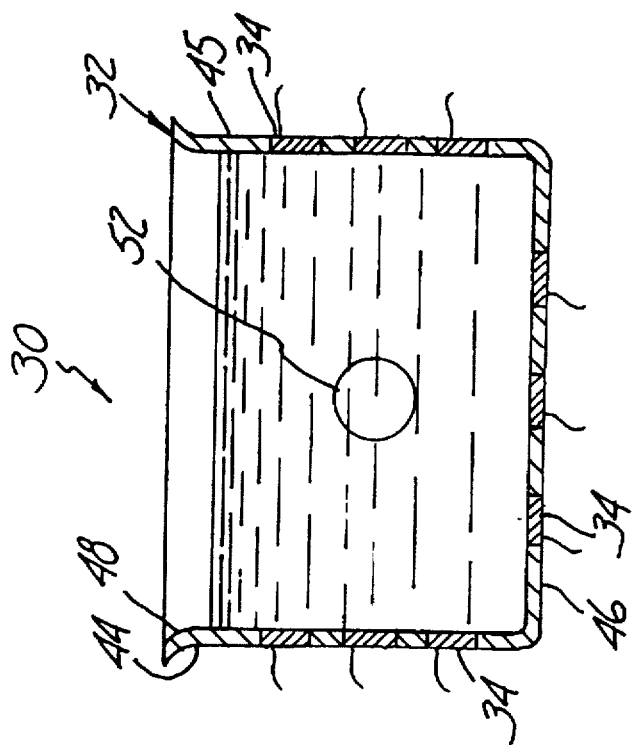
FIG. 2B is a cross-sectional view of the system of FIG. 2A.
Figure 2A:
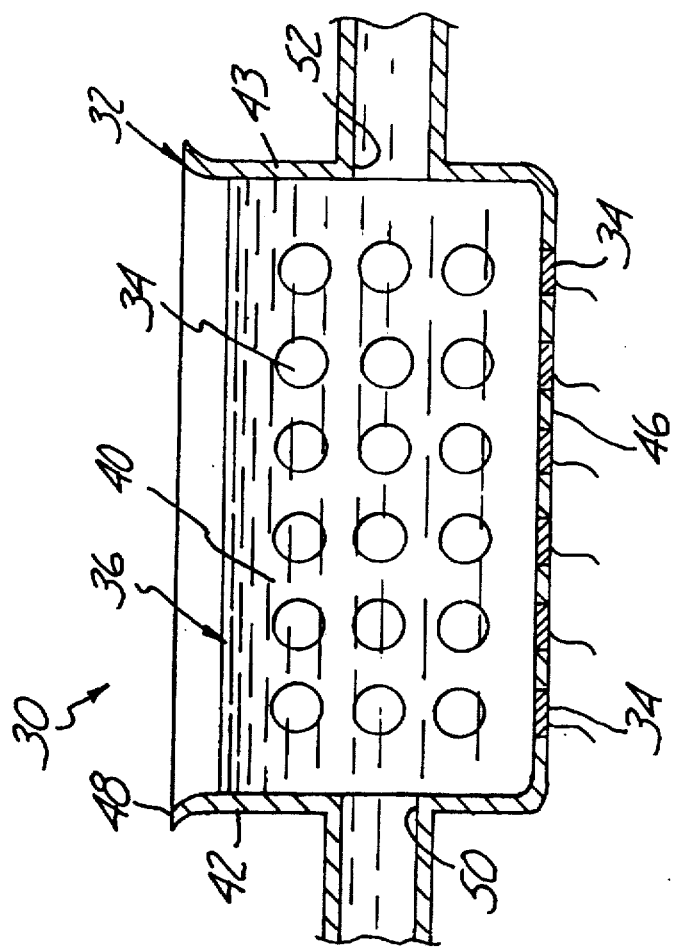
FIG. 2A is a cross-sectional view of an alternate embodiment of the system.

FIGS. 2A and 2B illustrate system 30 which is an alternate embodiment of system 10 shown in FIGS. 1A and 1B. System 30 includes reservoir 32 and transducers 34. Reservoir 32 is a generally rectangular-shaped vessel defining a fluid passage 36 having a sterilization region 40. Reservoir 32 generally includes end walls 42, 43, side walls 44, 45, floor 46 and upper portion 48. End walls 42, 43 define an inlet 50 and an outlet 52 through which the continuous flow of wastewater enters and exits reservoir 32, respectively. Inlet 50 and outlet 52 extend through end walls 42, 43 opposite one another and are in axial alignment with one another between floor 46 and upper portion 48. Upper portion 48 is located opposite floor 46 and opens upwardly for allowing temporary build-up or overflow of wastewater within reservoir 32. Upper portion 48 may alternatively be temporarily or permanently covered with a lid, cap or other temporary or permanent sealing or covering structures. Overall, end walls 42, side walls 44, floor 46 and upper portion 48 define a generally rectangular shaped flow passage 36 through which the continuous flow of wastewater flows across sterilization region 40 adjacent to transducers 34. Because flow passage 36 extends both above and below inlet 50 and outlet 52, flow passage 36 causes recirculation of portions of the continuous flow of wastewater and prolongs the retention of wastewater within sterilization region 40 adjacent transducers 34. The pooling or recirculation of the wastewater by flow passage 36 improves the effective sterilization of the continuous flow of wastewater while still permitting the continuous flow and discharge of wastewater required for the extremely large volumes of polluted water produced by manufacturing or production facilities.

Transducers 34 are similar to transducers 14. As with transducers 14, transducers 34 emit high frequency sound waves through and across the continuous flow of wastewater adjacent to sterilization region 40. Transducers 34 preferably emit sound waves having a frequency of between about 20 kilohertz to about 40 kilohertz to produce cavitation in the continuous flow of wastewater. Transducers 34 extend through floor 46 and side walls 44, 45 adjacent to sterilization region 40 of flow passage 36. Because transducers 34 are located along side walls 44, 45 and floor 46, transducers 34 emit high frequency sound waves from a plurality of directions through and across the continuous flow of wastewater within reservoir 32. Because the continuous flow of wastewater is exposed to high frequency sound waves from a plurality of different directions, cavitation within the continuous flow of wastewater is increased and system 30 more effectively kills bacteria within the continuous flow of wastewater. Because transducers 34 extend along and through floor 46 and side walls 44, 45, a large interior surface area of reservoir 32 and interior volume of reservoir 32 extends adjacent to or proximate transducers 34. Consequently, the sterilization region 40 adjacent to transducers 34 is larger for sterilizing and treating a larger volume of the continuous flow of wastewater for a longer period of time to more effectively kill bacteria within the continuous flow of wastewater.

Figure 3:
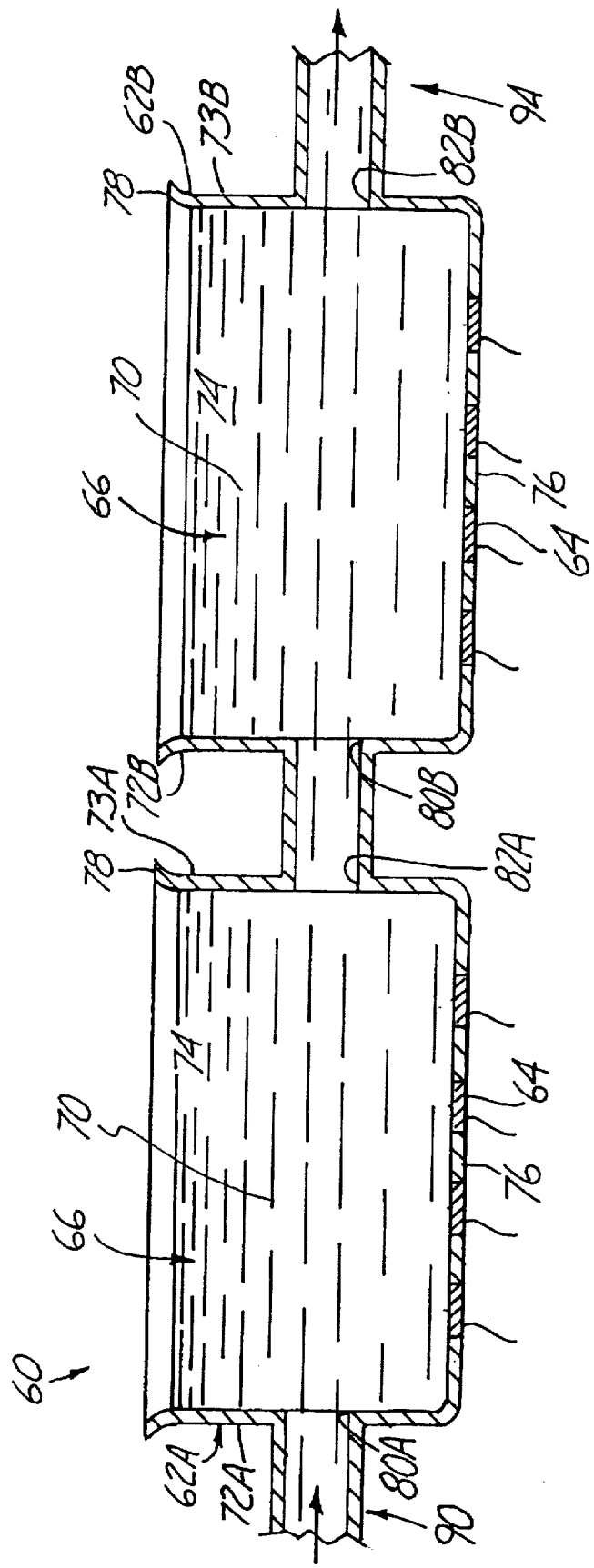
FIG. 3 is a cross-sectional view of an alternate embodiment of the system for treating a continuous flow of wastewater.

FIG. 3 illustrates system 60, an alternate embodiment of system 30 shown in FIGS. 2A and 2B. System 60 includes reservoirs 62A and 62B and transducers 64. Reservoirs 62A and 62B are interconnected in series so as to define a continuous flow passage 66 through reservoirs 62A and 62B. Reservoirs 62A and 62B are identical to one another and each include end walls 72A, 72B, 73A, 73B, side walls 74, floor 76 and upper portion 78, respectively. End walls 72A, 72B of reservoirs 62A, 62B define inlets 80A, 80B, respectively. End walls 73A, 73B of reservoirs 62A, 62B define outlets 82A, 82B, respectively. Inlet 80A extends through end wall 72A of reservoir 62A and is intermediate floor 76 and upper portion 78 of reservoir 62A. Outlet 82A extends through end wall 73A of reservoir 62A intermediate floor 76 and upper portion 78. Outlet 82A of reservoir 62A is preferably in axial alignment with inlet 80A and is in fluid communication with inlet 80B of reservoir 62B. Inlet 80B extends through side wall 72B of reservoir 62B opposite outlet 82B and is in fluid communication with outlet 82A of reservoir 62A so that fluid exiting reservoir 62A flows into reservoir 62B. Outlet 82B of reservoir 62B is opposite inlet 80B and extends through side wall 73B of reservoir 62B. Outlet 82B is located between floor 76 and upper portion 78 of reservoir 62B and is in axial alignment with inlet 80B.

High frequency transducers 64 are identical to high frequency transducers 34. Transducers 64 extend through floor 76 adjacent to fluid passage 66 and sterilization region 70 of reservoirs 62A, 62B. As with transducers 34, transducers 64 emit high frequency sound waves through and across the continuous flow of wastewater adjacent to sterilization region 70. Transducers 64 emit high frequency sound waves at a frequency of between about 10 kilohertz to about 200 kilohertz. Transducers preferably emit sound waves having a frequency of between about 20 kilohertz to about 40 kilohertz (20 kilohertz being the optimal) to produce cavitation in the continuous flow of wastewater.

In operation, the continuous flow of wastewater enters reservoir 62A through inlet 80A and flows into and across sterilization region 70 of fluid passage 66 defined within reservoir 62A. Because end walls 72A, 73A, side walls 74, floor 76 and upper portion 78 of reservoir 62A extend both above and below inlet 80A and outlet 82A, the continuous flow of wastewater temporarily recirculates within sterilization region 70 of reservoir 62A so that the continuous flow of wastewater is exposed to the high frequency sound waves emitted from high frequency transducers 64 within reservoir 62A for a longer period of time. As a result, a larger number of bacteria are killed by the high frequency sound waves. After the continuous flow of wastewater exits reservoir 62A through outlet 82A, the continuous flow of wastewater enters reservoir 62B through inlet 80B. Once again, the continuous flow of wastewater temporarily recirculates within reservoir 62B above and below inlet 80B and outlet 82B adjacent to and above transducers 64 of reservoir 62B. Consequently, the continuous flow of wastewater is exposed to the high frequency sound waves for a greater period of time within reservoir 62B before exiting reservoir 62B through outlet 82B and before being reused or released to the environment. Because reservoir 62A and 62B defines fluid passages 66 which are connected in series, the bacteria within the continuous flow of wastewater is more effectively destroyed and the continuous flow of wastewater is more effectively sterilized.

An experiment employing two reservoirs connected in series similar to system 60 resulted in a substantial reduction or elimination of bacteria within a continuous flow of wastewater. In the experiment, two reservoirs, each being identical to those illustrated in FIG. 3, were connected in series with one another to define a continuous fluid passage through both reservoirs. High frequency sound wave transducers extended through the floors of each of the reservoirs so as to communicate with wastewater flowing through each of the reservoirs. In particular, transducers each having a power rating of 35 to 40 watts, were located along the floor of each of the reservoirs. Each transducer had a diameter of approximately 30 millimeters and was spaced apart from adjacent transducers by approximately 10 centimeters. Each reservoir was 52 centimeters wide, 40 centimeters long and approximately 30 centimeters high. In accordance with the volume of each reservoir, the transducers of each reservoir had an overall power output of about one kilowatt. The transducers emitted sound waves with a frequency of about 20 kilohertz. Wastewater flowed into the first inlet of the first reservoir and out an outlet of the second reservoir at a rate of approximately three gallons per minute. Three tests were run using continuous flows of wastewater having different bacteria or different initial concentrations of bacteria. In each test, the number of bacteria within the continuous flow of wastewater was tested or sampled before the continuous flow of wastewater entered the first reservoir (illustrated by reference label 90 in FIG. 3) and after the wastewater exited the second reservoir (illustrated by reference label 94 in FIG. 3). Testing the continuous flow of wastewater for bacteria involved filling a petri dish at a selected point (locations 90 or 94) with a portion of the continuous flow of wastewater. A plurality of samples were then taken from each petri dish and averaged to estimate a total plate count of bacteria for the continuous flow of wastewater. The following chart illustrates the results of the experiment using a set-up substantially similar to system 60.

| | Test No. | Before Treatment (Location 90) | After Treatment (Location 94) |
|---|---|---|---|
| EXPERIMENTAL BACTERIAL COUNT BEFORE AND AFTER TREATMENT WITH HIGH FREQUENCY SOUND WAVES | | | |
| All Bacteria | 1 | TNTC* | TNTC* |
| Types (avg. | 2 | 780,000,000 | 320,000,000 |
| of 6 samples) | 3 | TNTC* | 520,000,000 |
| All Bacteria | 1 | TNTC* | 7,900,000,000 |
| Types (avg. | 2 | 5,200,000,000 | 780,000,000 |
| of 7 samples) | 3 | 6,800,000,000 | 1,800,000,000 |
| Coliform | 1 | 11,000,000 | 7,000,000 |
| Bacteria (avg. | 2 | 8,000,000 | 0 |
| of 6 samples) | 3 | 4,000,000 | 0 |

*TNTC = Too Numerous to Count

As illustrated in the above chart, a first series of tests was performed for all bacteria types with six samples taken from each petri dish and averaged to estimate a total plate count for bacteria within the continuous flow of wastewater prior to and after treatment by the high frequency sound waves. During a second series of tests for all bacteria types, seven samples were taken from each petri dish and averaged to estimate a total plate count for bacteria within the continuous flow of wastewater prior to and after treatment by the high frequency sound waves. In a third series of tests for coliform bacteria, six samples were taken from the petri dish and averaged to estimate a total plate count for coliform bacteria within the continuous flow of wastewater prior to and after treatment by the high frequency sound waves. Coliform bacteria is a substantial type of bacteria present in many kinds of bacteriologically polluted wastewater. As shown by the above chart, the third series of tests for coliform bacteria included three individual tests. In the first test, the continuous flow of wastewater had a coliform bacteria count of eleven million before treatment and a count of seven million after treatment. In the second and third tests for coliform bacteria, the continuous flows of wastewater had coliform bacteria counts of eight million and four million, respectively, before treatment. After treatment, substantially all of the coliform bacteria in the continuous flows of wastewater was eliminated to effectively sterilize the continuous flows of wastewater. As evidenced by the above test results, in each series of tests, the system of the present invention substantially reduced or completely killed the bacteria, including coliform bacteria, within the continuous flow of wastewater.

FIGS. 4A, 4B, 5A, 5B, 6A, 6B, 7A and 7B illustrate systems 100, 130, 160, and 200, respectively, which are alternate embodiments incorporating the present invention. Systems 100, 130, 160, and 200 are each designed for causing temporary recirculation of the continuous flow of wastewater within the reservoir to increase the amount of time required for the continuous flow of wastewater to flow through the reservoir adjacent the high-frequency transducers. In addition, systems 100, 130, 160, and 200 each disclose various inlet and outlet locations for increasing flow time through the reservoir, for increasing the number and overall power output of the transducers, and for preventing the buildup or accumulation of sediment along the floor of the reservoirs. Because systems 100, 130, 160, and 200 cause the continuous flow of wastewater to temporarily recirculate within the reservoirs, the continuous flow of wastewater requires a greater amount of time to flow through each reservoir. As a result, the continuous flow of wastewater is exposed for a greater amount of time to high-frequency sound waves from the transducers to more effectively kill bacteria. Because a greater number of transducers may be positioned adjacent to the continuous flow of wastewater, the overall power output of the transducers is increased to more effectively kill bacteria in the continuous flow of wastewater. Lastly, the prevention of sediment buildup along the floor reduces overall maintenance of the systems.

FIGS. 4A and 4B illustrate system 100, an alternate embodiment of system 30 shown in FIGS. 2A and 2B. For ease of illustration, those elements of system 100 which are similar to corresponding elements of system 30 are numbered similarly. System 100 includes reservoir 102 and high-frequency sound wave transducers 34. System 100 is similar to system 30 except that system 100 includes reservoir 102 in place of reservoir 32. Reservoir 102 is similar to reservoir 32 except that inlet 50 is replaced with inlet 120 and outlet 52 is replaced with outlet 122. Inlet 120 extends through end wall 42 opposite outlet 122 near upper portion 48. Outlet 122 extends through end wall 43 opposite inlet 120 near floor 46. Preferably, outlet 122 has an opening contiguously extending from floor 46 of reservoir 102. Because inlet 120 is located opposite outlet 122, the continuous flow of wastewater must flow horizontally across transducers 34. Because inlet 120 is located near upper portion 48 while outlet 122 is located near floor 46, inlet 120 and outlet 122 are vertically spaced opposite one another so that the continuous flow of wastewater must flow vertically across transducers 34 within reservoir 42. As a result, the continuous flow of wastewater requires a greater amount of time to flow through reservoir 42 and is exposed for a greater amount of time to high frequency sound waves from transducers 34 to more effectively kill bacteria within the continuous flow of wastewater. Alternatively, inlet 120 may be located near floor 46 while outlet 122 may be located near upper portion 48 so that inlet 120 and outlet 122 are vertically opposite one another. Because outlet 122 includes an opening which contiguously extends from floor 46, sediment along floor 46 is more easily moved with the continuous flow of wastewater through outlet 122. Consequently, the location of outlet 122 prevents the build-up of sediment adjacent floor 46 which would otherwise alter the frequency and amplitude characteristic of high frequency waves emitted by transducers 34 and the reduce the effectiveness of system 100 for treating and sterilizing the continuous flow of wastewater.

FIGS. 5A and 5B illustrate system 130, an alternate embodiment of system 100 shown in FIGS. 4A and 4B. For ease of illustration, those elements of system 130 which are the same as corresponding elements of system 100 are numbered similarly. System 130 includes reservoir 132 and transducers 134. Reservoir 132 is a generally rectangular shaped vessel defining a continuous rectangular shaped fluid passage 136 which forms a sterilization region 140. Reservoir 132 includes end walls 142, 143, side walls 44, floor 46 and upper portion 48. End wall 142 defines an inlet 150 and an outlet 152. Inlet 150 extends through end wall 142 near upper portion 48. Outlet 152 extends through end wall 142 near floor 46. Preferably, outlet 152 defines an opening which contiguously extends from floor 46 of reservoir 132. End wall 143 is located opposite end wall 142. Because inlet 150 and outlet 152 extend through the same wall, end wall 143 is capable of supporting additional transducers 134 along its surface area. Consequently, system 130 includes a greater concentration of transducers 134 with increased power to surround and encompass sterilization region 140. This larger concentration of transducers 134 and greater power output more effectively kills bacteria within the continuous flow of wastewater flowing through fluid passage 136.

Transducers 134 are similar to transducers 34. As with transducers 34, transducers 134 emit high frequency sound waves through and across a continuous flow of wastewater adjacent to sterilization region 140. Transducers 134 preferably emit sound waves having a frequency of between about 20 kilohertz to about 40 kilohertz to produce cavitation in the continuous flow of wastewater. Transducers 134 extend through floor 46, side walls 44 and end wall 143 adjacent to fluid passage 136 and sterilization region 140. Because transducers 134 are located along end wall 143, side walls 44, 45 and floor 46, transducers 134 emit high frequency sound waves from a plurality of directions through and across the continuous flow of wastewater within reservoir 132. Because the continuous flow of wastewater is exposed to high frequency sound waves from a plurality of different directions, cavitation within the continuous flow of wastewater is enhanced and system 130 more effectively kills bacteria within the continuous flow of wastewater.

In operation, the continuous flow of wastewater enters reservoir 132 through inlet 150 near upper portion 148. The continuous flow of wastewater substantially flows horizontally across reservoir 132, downward and along end wall 143 and again horizontally across reservoir 132 adjacent floor 46 until the continuous flow of wastewater exits reservoir 132 through outlet 152. Because of the limited size of inlet 150 and outlet 152, much of the continuous flow of wastewater will recirculate several times within reservoir 132 before exiting through outlet 152. Because inlet 150 is located near upper portion 148 while outlet 152 is located near floor 46, inlet 150 and outlet 152 are vertically opposite one another so that the continuous flow of wastewater must flow vertically across substantially the entire depth or height of reservoir 132. Because inlet 150 and outlet 152 extend through the same end wall 142, the continuous flow of wastewater must flow across a length or distance of reservoir 132 between end walls 142 and 143 a plurality of times before exiting through outlet 152. Because inlet 150 and outlet 152 are vertically spaced from one another, and because upper portion 48 extends above inlet 150, the continuous flow of wastewater tends to recirculate within reservoir 132. As a result, the continuous flow of wastewater requires a larger amount of time to flow through reservoir 132 before exiting reservoir 132 through outlet 152. Consequently, the continuous flow of wastewater is exposed to the high frequency sound waves emitted by transducers 132 for a greater amount of time to more effectively kill bacteria within the continuous flow of wastewater. Because outlet 152 defines an opening which preferably contiguously extends from floor 46, system 130 prevents sediment from building up along and adjacent to floor 46. Consequently, the effectiveness of transducers 134 along floor 46 is not reduced and maintenance of system 130 is minimized.

FIGS. 6A and 6B illustrate system 160, an alternate embodiment of system 130 shown in FIGS. 5A and 5B. System 160 includes reservoir 162 and transducers 164. Reservoir 162 is a generally rectangular vessel defining a fluid passage 166 having a sterilization region 170. Reservoir 162 generally includes end walls 172, 173, side walls 174, 175, floor 176 and upper portion 178. End wall 172 defines an inlet 180 through which the continuous flow of wastewater enters reservoir 162. Inlet 180 extends through end wall 172 between floor 176 and upper portion 178. Preferably inlet 180 is located towards upper portion 178. Floor 176 defines outlet 182 through which the continuous flow of wastewater exits reservoir 162. Outlet 182 preferably extends through floor 176 between side walls 174, 175 and end walls 172, 173. Because end walls 172 and 173 extend above and below inlet 180 and because floor 176 extends around and beyond outlet 182, reservoir 162 causes the continuous flow of wastewater entering through inlet 180 and exiting through outlet 182 to pool within sterilization region 170 of flow passage 166 to prolong the period of time the continuous wastewater is exposed to high frequency sound waves emitted by transducers 164.

Transducers 164 are similar to transducers 134. As with transducers 134, transducers 164 emit high frequency sound waves through and across a continuous flow of wastewater adjacent to sterilization region 170. Transducers 164 preferably emit sound waves having a frequency of between about 20 kilohertz to about 40 kilohertz to produce cavitation in the continuous flow of wastewater. Transducers 164 extend through side walls 174, 175, end wall 173 and floor 176 about outlet 182 adjacent to sterilization region 170 of flow passage 166. Because transducers 164 are located on side walls 174, end wall 173 and floor 176 of reservoir 162, sound waves are emitted from a plurality of different directions through the continuous flow of wastewater flowing through and across sterilization region 170 of flow passage 166. Because the continuous flow of wastewater containing the bacteria is exposed to high frequency sound waves from a plurality of different directions, transducers 164 produce a larger degree of cavitation which more effectively kills bacteria within the wastewater. Because transducers 164 extend through side walls 174, end wall 173 and floor 176, a large interior surface area of reservoir 162 and interior volume of reservoir 162 extends adjacent to or proximate one of transducers 164. Consequently, the sterilization region 170 defined by transducers 164 is larger for sterilizing and treating a larger volume of continuous flow of wastewater for a longer period of time to more effectively kill bacteria within the continuous flow of wastewater.

Figure 7B:
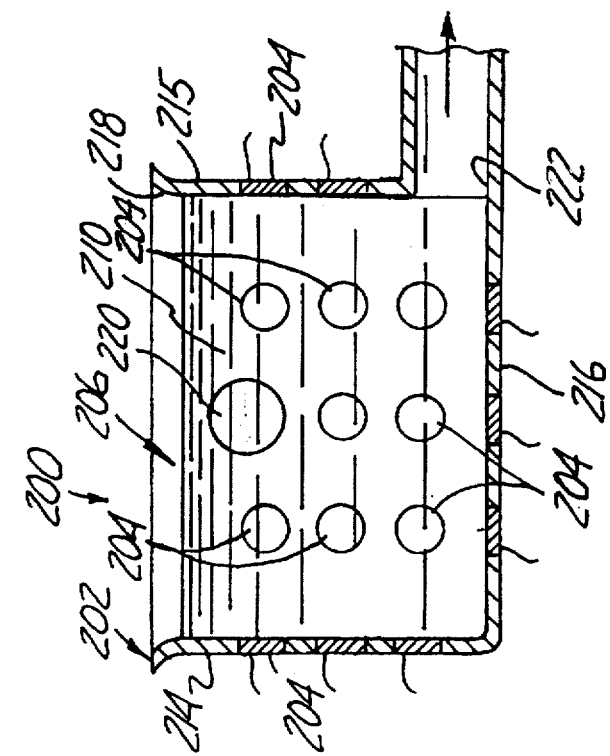
FIG. 7B is a cross-sectional view of the system of FIG. 7A.
Figure 7A:
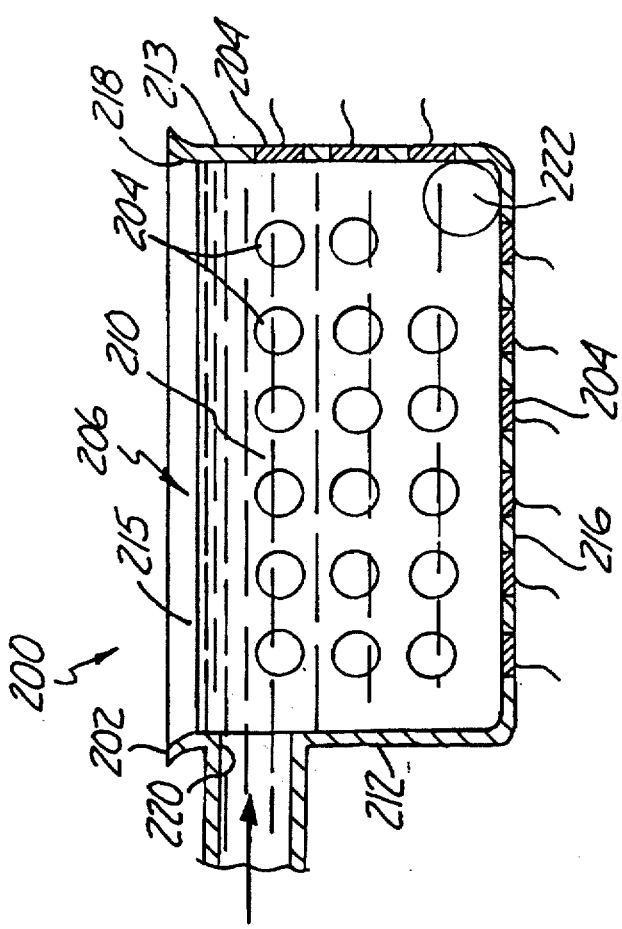
FIG. 7A is a cross-sectional view of an alternate embodiment of the system.

FIGS. 7A and 7B illustrate system 200, an alternate embodiment of system 130 shown in FIGS. 5A and 5B. System 200 includes reservoir 202 and transducers 204. Reservoir 202 is a generally rectangular vessel defining a fluid passage 206 having a sterilization region 210. Reservoir 202 generally includes end walls 212, 213, side walls 214, 215, floor 216 and upper portion 218. End wall 212 defines an inlet 220 through which the continuous flow of wastewater enters reservoir 202. Inlet 220 extends through end wall 212 between floor 216 and upper portion 218. Preferably, inlet 220 is located towards upper portion 218 to increase the distance across which the continuous flow of wastewater must traverse before exiting through outlet 222. Outlet 222 extends through side wall 215 near floor 216. Preferably, outlet 222 defines an opening contiguously extending from floor 216 to prevent the accumulation of sediment and other particles along floor 216. Because inlet 220 is preferably located near upper portion 218 while outlet 222 extends from floor 216 and through side wall 214, the continuous flow of wastewater must flow diagonally down and across substantially all of transducers 204 before exiting reservoir 202. Consequently, reservoir 202 retains the continuous flow of wastewater for a longer period of time within sterilization region 210 to more effectively kill bacteria within the continuous flow of wastewater. Because end walls 212 and 213 extend above and below inlet 220 and because side walls 214, 215 extend above outlet 222, the continuous flow of wastewater tends to pool within reservoir 202. The recirculation of the wastewater by reservoir 202 further increases the effectiveness at which system 200 kills bacteria in the continuous flow of wastewater.

Transducers 204 are similar to transducers 134 of system 130. Transducers 204 extend through end wall 213, side walls 214, 215 and floor 216 adjacent to sterilization region 210. As with transducers 134, transducers 204 emit high frequency sound waves through and across a continuous flow of wastewater adjacent to sterilization region 210. Transducers 204 preferably emit sound waves having a frequency of between about 20 kilohertz to about 40 kilohertz to produce cavitation in the continuous flow of wastewater. Because transducers 204 are located along end wall 213, side walls 214, 215 and floor 216, transducers 204 emit high frequency sound waves from a plurality of directions through and across the continuous flow of wastewater within reservoir 202. Because the continuous flow of wastewater is exposed to high frequency sound waves from a plurality of different directions, cavitation within the continuous flow of wastewater is increased and system 200 more effectively kills bacteria within the continuous flow of wastewater.

As can be appreciated, the wastewater treatment system of the present invention may have a variety of shapes and configurations, a variety of different high frequency sound wave transducer mechanisms, a variety of different high frequency sound wave transducer locations and a variety of inlet and outlet locations which regulate the flow rate of the continuous flow of wastewater or promote recirculation to effectively kill bacteria within the continuous flow of wastewater. For example, although depicted as extending through the walls of reservoirs 32, 62A, 62B, 102, 132, 162 and 202, the transducers of the present invention may alternatively comprise immersible transducer units or modular components bolted or otherwise mounted to the walls within the reservoirs. Immersible transducer components are conventionally known and are supplied by Branson Ultrasonics Corporation of Danbury, Conn. Immersible ultrasonic transducers typically include a multitude of individual transducers hermetically sealed within a modular component. The modular components are capable of being immersed in liquid and otherwise mounted to the walls or bottom of a tank or reservoir. Furthermore, the high frequency sound wave transducers utilized in reservoirs 32, 62A, 62B, 102, 132, 162 and 202 may also additionally or alternatively extend through the walls of the reservoirs that define the inlets and the outlets of the respective reservoirs, adjacent or around the respective inlets and outlets, to further increase the directions at which high frequency sound waves are emitted through the continuous flow of wastewater to treat and sterilize the continuous flow of wastewater.

Moreover, the means by which wastewater is input into each reservoir and the memos by which the treated wastewater is removed from each reservoir may utilize a variety of structural or mechanical water flow devices. For example, each inlet may alternatively comprise a channel or piping which fills a reservoir through the upward opening defined by the upper portion of the reservoir. Similarly, the outlet may alternatively comprise any channel or piping by which the continuous flow of wastewater may be continuously withdrawn from the reservoir. For example, the outlet may alternatively comprise piping introduced into the reservoir through the opening defined by the upper portion of the reservoir whereby the continuous flow of wastewater is siphoned or withdrawn from the reservoir by pumping means or gravity.

In addition to killing bacteria for treating and sterilizing a continuous flow of wastewater, the above method and apparatus may also be separately used to catalyze reactions within a continuous flow of liquid containing reactants. It has been discovered that the cavitation caused by the high frequency sound waves catalyze reactions within the continuous flow of liquid. As a result, the need for additional chemical or other catalysts is reduced or eliminated.

Although the present invention has been described with reference to preferred embodiments, workers skilled in the art will recognize that changes may be made in form and detail without departing from the spirit and scope of the invention.

What is claimed is:

1. An apparatus for sterilizing a continuous flow of wastewater, the apparatus comprising:
   a fluid passage through which the continuous flow of wastewater passes, the fluid passage defining a closed chamber having at least one side wall and a pair of opposing end walls, extending upward from the floor, and the floor being opposed to the cover, the chamber having an inlet and an outlet through which the continuous flow of wastewater enters and exits the chamber; and
   a plurality of transducers for emitting high frequency sound waves having a frequency of about 10 to 200 kiloHertz into the continuous flow of wastewater to cause cavitation in the wastewater to kill the bacteria include:
      a first plurality of transducers connected to the side wall and oriented to emit ultrasonic waves generally parallel to a first axis aligned transverse to the continuous fluid flow path;
      a second plurality of transducers connected to each of the end walls and oriented to emit ultrasonic waves generally parallel to a second axis, the second axis being aligned perpendicular to the first axis and generally parallel to the continuous fluid flow path; and
      a third plurality of transducers connected to the side wall and oriented to emit ultrasonic waves generally parallel to a third axis, the third axis being perpendicular to the first axis and to the second axis and being tranverse to the continuous fluid flow path,
      wherein the ultrasonic waves emitted along the first, second and third axes converge in the wastewater as it passes through the chamber to intensify cavitation in the wastewater.

2. The apparatus of claim 1 wherein the pair of end walls define a first end wall and a second end wall, and the inlet is located on the first end wall and the outlet is located on the second end wall opposite the inlet with the inlet being spaced vertically from the outlet.

3. The apparatus of claim 1 wherein the inlet and the outlet are connected to the same end wall.

4. The apparatus of claim 1 wherein at least a portion of the outlet contiguously extends from the side wall of the chamber.

5. The apparatus of claim 1 wherein the inlet is located on one of the end walls and the outlet is located on the side wall, the inlet being spaced vertically from and above the outlet.

6. A method for sterilizing a continuous flow of wastewater containing bacteria, the method comprising:
   providing a continuous flow of wastewater containing bacteria in a fluid passageway; and
   directing high frequency sound waves into the continuous flow of wastewater at a power level and for a period of time sufficient to cause cavitation in the wastewater to kill the bacteria, the directing of the sound waves including:
      directing ultrasound waves in a first direction into the wastewater flow generally parallel to a first axis, the first axis being aligned transverse to the wastewater flow;
      directing ultrasound waves in a second direction into the wastewater flow generally parallel to a second axis, the second axis being perpendicular to the first axis and being aligned generally parallel to wastewater flow; and
      directing ultrasound waves in a third direction into the wastewater flow along a third axis, the third axis being perpendicular to the first and second axes and being aligned transverse to the wastewater flow.
   wherein the waves directed generally parallel to the first, second, and third axes converge in the wastewater flow in the fluid passageway to intensify cavitation of the wastewater.

7. The method of claim 6 wherein the high frequency sound waves applied to the continuous flow of wastewater have a frequency of about 10 kilohertz to about 200 kilohertz.

8. The method of claim 6 wherein the directing steps further include:
   directing ultrasound waves into the wastewater flow generally parallel to the first axis in a fourth direction opposite the first direction;
   directing ultrasound waves into the wastewater flow generally parallel to the second axis in a fifth direction opposite the second direction; and directing ultrasound waves into the wastewater flow generally parallel to the third axis in a sixth direction opposite the third direction, wherein the ultrasound waves directed along the first, second, third, fourth, fifth and sixth directions converge in the wastewater flow to intensify cavitation of the wastewater.

9. A method for sterilizing a continuous flow of wastewater containing bacteria, the method comprising:

providing a continuous flow of wastewater in a fluid passageway; and directing high frequency sound waves into the continuous flow of wastewater to cause cavitation in the wastewater to kill the bacteria, the directing step further including:

directing ultrasound waves in a first and second direction into the wastewater flow, the first direction being diametrically opposite the second direction;

directing ultrasound waves in a third direction and a fourth direction into the wastewater flow, the third and fourth directions being diametrically opposed to each other and being at a 90° angle relative to the first and second directions; and directing ultrasound waves in a fifth and sixth direction into the wastewater flow, the fifth and sixth directions being diametrically opposed to each to other and being at a 90° angle relative to the first direction and second directions and at a 90° angle relative to the third and fourth directions.

* * * * *

UNITED STATES PATENT AND TRADEMARK OFFICE
CERTIFICATE OF CORRECTION

PATENT NO. : 5,611,993
DATED : March 18, 1997
INVENTOR(S) : Eilaz Piri Ogly Babaev It is certified that error appears in the above-indentified patent and that said Letters Patent is hereby corrected as shown below:

Col. 11, line 23, delete "memos", insert --means--

Col. 11, lines 56 and 57, after "end walls", delete "extending upward from the floor, and the floor being opposed to the cover,".

Col. 12, line 52, after "flow", delete ".", insert --,--

Signed and Sealed this

First Day of July, 1997

Attest:

Attesting Officer

BRUCE LEHMAN

Commissioner of Patents and Trademarks